US007429376B2

(12) United States Patent
Ildstad

(10) Patent No.: US 7,429,376 B2
(45) Date of Patent: Sep. 30, 2008

(54) METHODS OF SCREENING FOR COMPOUNDS THAT IMPROVE ENGRAFTMENT

(75) Inventor: Suzanne T. Ildstad, Prospect, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 29 days.

(21) Appl. No.: 11/253,296

(22) Filed: Oct. 17, 2005

(65) Prior Publication Data

US 2006/0160107 A1    Jul. 20, 2006

Related U.S. Application Data

(60) Provisional application No. 60/619,332, filed on Oct. 15, 2004.

(51) Int. Cl.
*A61K 48/00* (2006.01)
*C12N 5/08* (2006.01)
*C12P 19/34* (2006.01)

(52) U.S. Cl. .................... 424/93.21; 435/91.2; 435/370; 514/12

(58) Field of Classification Search ........................ None
See application file for complete search history.

(56) References Cited

U.S. PATENT DOCUMENTS

| 5,772,994 A | 6/1998 | Ildstad et al. | |
|---|---|---|---|
| 6,013,519 A | 1/2000 | Ildstad et al. | |
| 2002/0094327 A1* | 7/2002 | Petersen | 424/93.21 |

OTHER PUBLICATIONS

Huang et al., "Promotion of Chimerism and Tolerance by Flt3 Ligand-Mobilized Facilitating Cells Is Associated with Upregulation of CXCR4 and SDF-1," Blood (ASH Annual Meeting Abstracts), 2004, vol. 104, abstract 1286.*
Billingham, "Pathology and etiology of chronic rejection of the heart," *Clin. Transplant.*, 1994, 8:289-292.
Broxmeyer et al., "Effects of CC, CXC, C, and $CX_3C$ Chemokines on Proliferation of Myeloid Progenitor Cells, and Insights into SDF-1-Induced Chemotaxis of Progenitors," *Ann. N.Y. Acad. Sci.*, 1999, 872:142-162.
Chilton et al., "Hematopoietic stem cells from NOD mice exhibit autonomous behavior and a competitive advantage in allogeneic recipients," *Blood*, 2005, 105:2189-2197.
Colson et al., "Absence of clinical GVHD and the in vivo induction of regulatory T cells after transplantation of facilitating cells," *Blood*, 2004, 104:3829-3835.
Davenport and Ildstad, "The Role of the Facilitating Cell in the Establishment of Donor Chimerism and Transplantation Tolerance," *Clin. Biochem.*, 1998, 31(5):359-367.
Frenette et al., "Endothelial selectins and vascular cell adhesion molecule-1 promote hematopoietic progenitor homing to bone marrow," *Proc. Natl. Acad. Sci. USA*, 1998, 95:14423-14428.
Fugier-Vivier et al., "Plasmacytoid precursor dendritic cells facilitate allogeneic hematopoietic stem cell engraftment," *J. Exp. Med.*, 2005, 201(3):373-383.
Grimes et al., "Graft facilitating cells are derived from hematopoietic stem cells and functionally require CD3, but are distinct from T lymphocytes," *Exp. Hematol.*, 2004, 32:946-954.
Huang et al., "FL-mobilized peripheral blood but not FL-expanded bone marrow FC promote establishment of chimerism and tolerance," *Stem Cells*, 2005, published online, 44 pages.
Huang et al., "Matching at the MHC class I K locus is essential for long-term engraftment of purified hematopoietic stem cells: a role for host NK cells in regulating HSC engraftment," *Blood*, 2004, 104:873-880.
Huang et al., "NK Cells Play a Critical Role in the Regulation of Class I-Deficient Hemopoietic Stem Cell Engraftment: Evidence for NK Tolerance Correlates with Receptor Editing," *J. Immunol.*, 2005, 175:3753-3761.
Jacquet et al., "Facilitating cells as a venue to establish mixed chimerism and tolerance," *Pediatr. Transplant.*, 2003, 7(5):348-357.
Kaufman et al., "Phenotypic Characterization of a Novel Bone Marrow-Derived Cell That Facilitates Engraftment of Allogeneic Bone Marrow Stem Cells," *Blood*, 1994, 84(8):2436-2446.
Neipp et al., "A partial conditioning approach to achieve mixed chimerism in the rat: depletion of host natural killer cells significantly reduces the amount of total body irradiation required for engraftment," *Transplantation*, 1999, 68(3):369-378.
Reca et al., "Functional receptor for C3a anaphylatoxin is expressed by normal hematopoietic stem/progenitor cells, and C3a enhances their homing-related responses to SDF-1," *Blood*, 2003, 101:3784-3793.
Simmons et al., "Adhesion molecules in haemopoiesis," *Baillires Clin. Haematol.*, 1997, 10(3):485-505.
Verfaillie, "Adhesion Receptors as Regulators of the Hematopoietic Process," *Blood*, 1998, 92:2609-2612.
Verfaillie et al., "Purified Primitive Human Hematopoietic Progenitor Cells with Long-Term In Vitro Repopulating Capacity Adhere Selectively to Irradiated Bone Marrow Stroma," *J. Exp. Med.*, 1990, 172:509-520.
Wakkach et al., "Characterization of Dendritic Cells that Induce Tolerance and T Regulatory 1 Cell Differentiation In Vivo," *Immunity*, 2003, 18:605-617.
Xu et al., "Production of Donor T Cells Is Critical for Induction of Donor-Specific Tolerance and Maintenance of Chimerism," *J. Immunol.*, 2004, 172:1463-1471.

* cited by examiner

*Primary Examiner*—Teresa Strzelecka
*Assistant Examiner*—Molly E Baughman
(74) *Attorney, Agent, or Firm*—Fish & Richardson P.C.

(57) ABSTRACT

The invention provides for methods of screening for compounds that increase the expression of P-selectin, SDF-1, and/or CXCR4 on facilitatory cells (FCs). The invention also provides for methods of screening for compounds that increase the level of p-predendritic cells (p-pre DC) without substantially decreasing the level of natural killer (NK) cells in a population of FCs. The invention further provides for methods of characterizing the facilitating capability of FCs by evaluating such cells for the amount of P-selectin, SDF-1, and/or CXCR4.

5 Claims, 7 Drawing Sheets

A

B

METHODS OF SCREENING FOR COMPOUNDS THAT IMPROVE ENGRAFTMENT

CROSS REFERENCE TO RELATED APPLICATIONS

This application claims priority under 35 U.S.C. §119(e) of U.S. Application No. 60/619,332, filed Oct. 15, 2004.

FEDERALLY SPONSORED RESEARCH OR DEVELOPMENT

The U.S. Government has certain rights in this invention pursuant to Grant No. HL63442 awarded by the National Institute of Health.

TECHNICAL FIELD

This invention relates to improving engraftment, and more particularly to screening for compounds that improve engraftment.

BACKGROUND

Bone marrow transplantation (BMT) offers great promise for the treatment of a number of chronic disease states, including autoimmunity, organ tolerance, and the hemoglobinopathies. Widespread clinical application of this approach, however, is dependent upon the development of methods to establish and maintain chimerism and avoid graft-versus-host disease (GVHD).

Facilitating cells (FCs) are a $CD8^+/TCR^-$ bone marrow subpopulation that enhance engraftment of purified hematopoietic stem cells (HSC) in allogeneic recipients without causing GVHD. FCs also potently enhance engraftment of suboptimal numbers of HSC in syngeneic recipients. Therefore, approaches to expand FC numbers and enhance their function could have a significant impact upon the use of BMT in treating nonmalignant disorders, especially when HSC numbers are limiting such as in cord blood transplantation.

SUMMARY

In one aspect, the invention provides methods of screening for a compound that increases the amount of SDF-1 polypeptide or mRNA encoding the SDF-1 polypeptide in facilitatory cells (FCs). Such a method includes contacting FCs with a test compound; and determining the amount of SDF-1 polypeptide or mRNA encoding SDF-1 polypeptide in the FCs. Generally, an increase in the amount of SDF-1 polypeptide or mRNA encoding SDF-1 polypeptide in FCs contacted with the test compound compared to an amount of SDF-1 polypeptide or mRNA encoding SDF-1 polypeptide in FCs not contacted with the test compound is indicative of a compound that increases the amount of SDF-1 polypeptide or mRNA encoding the SDF-1 polypeptide in the FCs.

In another aspect, the invention provides methods of screening for a compound that increases the amount of CXCR4 polypeptide or mRNA encoding the CXCR4 polypeptide in FCs. Such a method includes contacting stem cells or FCs with a test compound; and determining the amount of CXCR4 polypeptide or mRNA encoding CXCR4 polypeptide in the FCs. Typically, an increase in the amount of CXCR4 polypeptide or mRNA encoding CXCR4 polypeptide in FCs contacted with the test compound compared to an amount of CXCR4 polypeptide or mRNA encoding CXCR4 polypeptide in FCs not contacted with the test compound is indicative of a compound that increases the amount of CXCR4 polypeptide or mRNA encoding CXCR4 polypeptide in the FCs.

In still another aspect, the invention provides for methods of screening for a compound that increases the amount of P-selectin polypeptide or mRNA encoding the P-selectin polypeptide in FCs. Such a method includes contacting FCs with a test compound; and determining the amount of P-selectin polypeptide or mRNA encoding the P-selectin polypeptide in the FCs. Generally, an increase in the amount of P-selectin polypeptide or mRNA encoding the P-selectin polypeptide in FCs contacted with the test compound compared to an amount of P-selectin polypeptide or mRNA encoding the P-selectin polypeptide in FCs not contacted with the test compound is indicative of a compound that increases the amount of P-selectin polypeptide or mRNA encoding the P-selectin polypeptide in the FCs.

The determining step of such methods can be a nucleic acid-based method such as RT-PCR. Alternatively, the determining step can be polypeptide based such as an immunoassay.

In yet another embodiment, the invention provides methods of screening for a compound that improves the ability of donor FCs to facilitate engraftment of cells or tissue into a recipient. Such a method includes contacting a population of FCs with a test compound; and determining the level of precursor-plasmacytoid dendritic cells (p-pre DC) in the population of FCs. Typically, an increase in the level of p-preDCs in the population of FCs contacted with the test compound compared to a level of p-preDCs in a population of FCs not contacted with the test compound is indicative of a compound that improves the ability of donor FCs to facilitate engraftment. Such a method also can include determining the level of natural killer (NK) cells in the population of FCs. Usually, the lack of a substantial decrease in the level of NK cells in the population of FCs contacted with the test compound compared to a level of NK cells in a population of FCs not contacted with the test compound is indicative of a compound that that improves the ability of donor FCs to facilitate engraftment.

In another aspect, the invention provides methods of characterizing the facilitating capability of FCs. Such a method includes determining the level of at least one marker such as SDF-1 polypeptide, mRNA encoding the SDF-1 polypeptide, CXCR4 polypeptide, mRNA encoding the CXCR4 polypeptide, P-selectin polypeptide, or mRNA encoding the P-selectin polypeptide; and characterizing the facilitating capability of the FCs based on the determining step.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1:
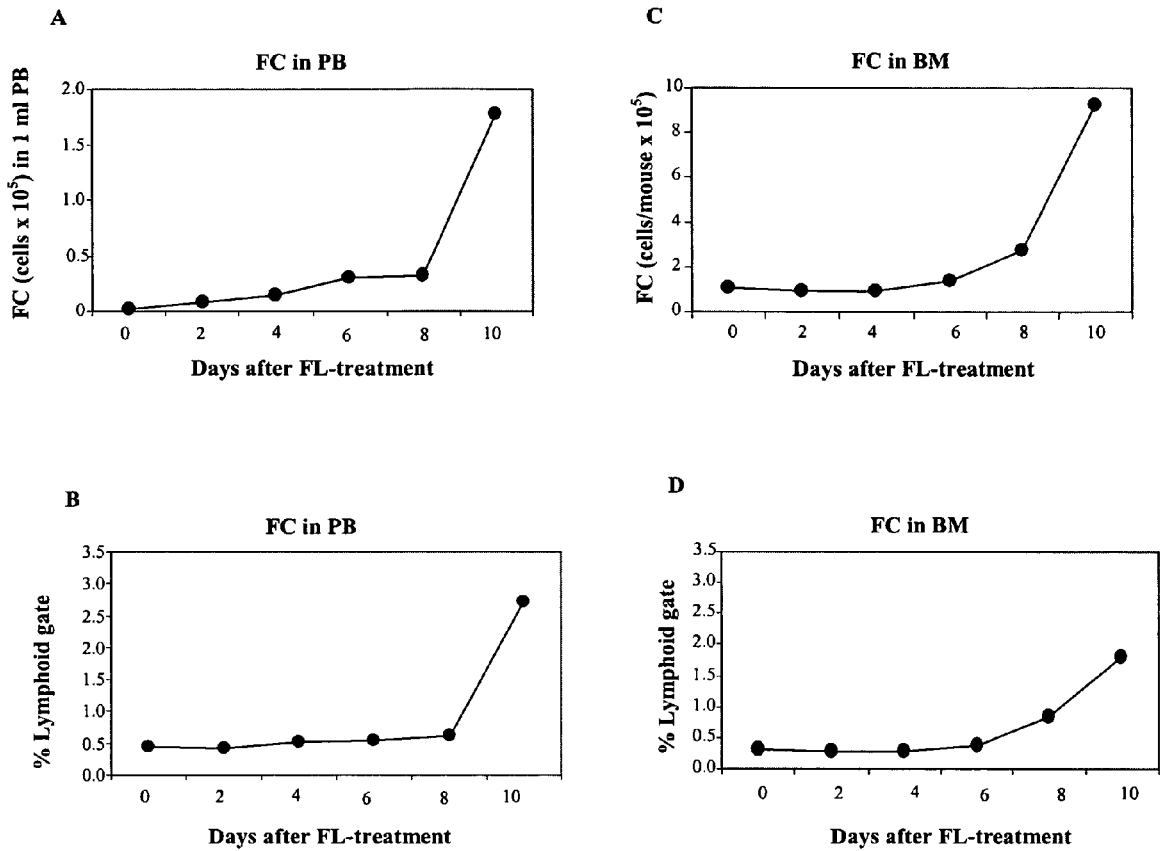
FIG. 1. Kinetics and composition of FL-expanded FC in PB or BM. PB was obtained daily and PBMC were counted. The FC (CD8$^+$/TCR$^-$) was analyzed by flow cytometry, and the absolute number of FC cells per mouse after harvest from femur and tibia in BM was calculated based on the total number of BM cell counts (C) or FC cells/μl of peripheral blood (A) was calculated based on PBMC counts, and percentage of FC in BM and PB (D and B) were based on the lymphoid gate. The results are representative of two separate experiments (n=4 animals per group).

In the present studies, functional capability of FCs to facilitate engraftment was evaluated after mobilization following expansion with a tolerogenic-promoting growth factor. Growth factor-expanded FCs from peripheral blood (PB) exhibited enhanced function, in striking contrast to FCs from bone marrow (BM), which were significantly impaired in function. Experiments herein demonstrate that chimeras prepared with growth factor-expanded PB FCs exhibited donor-specific transplantation tolerance to skin grafts and did not develop GVHD. The results reported herein herein have important implications in the development of novel cell-based strategies to immunomodulate a donor and a recipient, as well as in approaches for ex vivo manipulation of donor HSC to potentiate engraftment and tolerance yet avoid GVHD.

Adhesion molecules play a major role in HSC homing and migration. Therefore, the adhesion molecules associated with FCs were examined. Experiments herein determined that P-selectin expression was significantly up-regulated on growth factor-expanded PB FCs compared to growth factor-expanded BM FCs, while the expression of VCAM-1 was downregulated on growth factor-expanded PB FCs. Cell surface expression of other adhesion molecules that influence homing and engraftment was relatively unchanged. Based on these results, the upregulation of P-selectin combined with downregulation of VCAM-1 on growth factor-expanded PB FCs may enhance mobilization and subsequent homing to the BM, suggesting that FCs serve as a chaperone cell for enhancing HSC migration. These findings may be clinically important because ex vivo manipulation of cell-based therapies to optimize outcome by enhancing expression of these molecules could allow enhanced potency as well as preserve in vivo function.

In addition to adhesion molecules, trafficking of HSC also is regulated by chemokines. The outcome of HSC transplantation is influenced by the ability of the cells to home and repopulate specialized BM niches. Crosstalk between HSC and the microenvironment results in a series of highly regulated events involving interplay between chemokines, growth factors, proteolytic enzymes, and adhesion molecules. Strikingly, the enhanced engraftment-potential of PB FCs was associated with significant up-regulation of transcripts for the chemokine, SDF-1, and its receptor, CXCR4, compared to unexpanded FCs and growth factor-expanded BM FCs. The data reported herein suggest a collaborative role for FCs in enhancing HSC homing and migration during mobilization and after transplantation. Based on the results reported herein, FCs may act as a collaborative cell to chemoattract and chaperone HSC to the hematopoietic microenvironment after transplantation. For example, the SDF-1 produced by the FCs may chemoattract the HSC and simultaneously exert an anti-apoptotic effect. Therefore, enhanced adhesion could increase the efficiency of the migration process following transplantation.

The invention provides for methods of screening for compounds that enhance or preserve expression of chemokines and adhesion molecules critical to homing. The compounds identified by the methods disclosed herein may allow the current limitations to BMT to be overcome. The methods disclosed herein include, but are not limited to, screening for a compound that increases the amount of SDF-1 polypeptide or mRNA encoding said SDF-1 polypeptide in FCs or screening for a compound that increases the amount of CXCR4 polypeptide or mRNA encoding said CXCR4 polypeptide in FCs.

To screen for compounds that have a desired biological effect on FCs, FCs are first contacted with a test compound. FCs and methods of enriching or purifying FCs have been described. See, for example, U.S. Pat. Nos. 5,772,994; and 6,013,519; Kaufman et al., 1994, *Blood*, 84(8):2436-46; Davenport & Ildstad, 1998, *Clin. Biochem.*, 31(5):359-67; Jacquet et al., 2003, *Pediatr. Transplant.*, 7(5):348-574; Grimes et al., 2004, *Exp. Hematol.*, 32:946-954; and Colson et al., 2004, *Blood*, 104:3829-3835. As used herein, compounds can include, without limitation, any organic or inorganic compound including polypeptides, nucleic acids, lipids, polysaccharides, carbohydrates, chemical products, plant extracts, antibodies, enzymes, growth factors, hormones, vitamins, minerals, or any mixture or derivatives thereof. Compounds used in the methods of the invention may be natural compounds or synthetic compounds. Representative examples of compounds that can be used to screen for the desired activity can be found, for example, in the Sigma-Aldrich Chemical Company catalog (St. Louis, Mo.).

After a population of FCs has been contacted with a test compound under appropriate conditions (e.g., 37° C.), the population of cells are analyzed for the amount of SDF-1 polypeptide or mRNA encoding said SDF-1 polypeptide or the amount of CXCR4 polypeptide or mRNA encoding said CXCR4 polypeptide. Increases in the amount of polypeptide or corresponding mRNA can be determined by those of skill in the art. For example, mRNA transcripts can be detected by Northern blotting or RT-PCR. See, for example, Sambrook et al., 1989, *Molecular Cloning: A Laboratory Manual*, Cold Spring Harbor Laboratories, New York, N.Y. Immunoassay formats such as those disclosed herein (ELISA, immunoprecipitation-mass spectrometry (IP-MS), and Western blots) can be used to detect the polypeptide product of the heterologous nucleic acid molecule and are well known in the art. See, *Short Protocols in Molecular Biology*, Ch. 11, John Wiley & Sons, Ed., Ausubel et al., 1992. In addition to ELISA, solid-phase immunoassays include competition immunoassays, immobilized-antigen immunoassays, immobilized-antibody immunoassays, and double-antibody immunoassays. Further, several types of mass spectrometry (MS) are available and routinely used in the art, and include Fourier-transform MS, Ion-trap MS, Magnetic-sector MS, Quadropole MS and Time-of-flight (TOF) MS.

Detection of nucleic acids or polypeptides in vitro or in vivo is usually via a label, e.g., a radioactive label (e.g., $^3$H, $^{125}$I, $^{131}$I, $^{32}$P, $^{35}$S, and $^{14}$C) or a non-radioactive label (e.g., a fluorescent label, a chemiluminescent label, a paramagnetic label, or an enzyme label) using techniques known to those of ordinary skill in the art. Examples of enzyme labels used routinely in the art for detection and quantitation include horseradish peroxidase (HRP) and alkaline phosphatase (AP). The substrates available for either HRP or AP labels are known in the art and can be selected based upon the desired method of detecting complex formation (e.g., a fluorogenic, chemiluminescent or colorimetric signal).

Generally, a test compound is a candidate for further analysis when an increase in the amount of SDF-1 polypeptide, CXCR4 polypeptide, or mRNA encoding SDF-1 or CXCR4 polypeptides in FCs following contact with a test compound is observed relative to the amount of the polypeptide or mRNA in FCs not contacted with said test compound.

The methods disclosed herein also include screening for a compound that improves the ability of donor FCs to facilitate engraftment of cells or tissue into a recipient. As described above, FCs are first contacted with a test compound under appropriate conditions, and the level of precursor-plasmacytoid dendritic cells (p-pre DCs) in the population of FCs are determined. P-pre DC cells are known in the art, and can be detected and identified using routine procedures such as FACS analysis. See, for example, Fugier-Vivier et al., 2005, *J. Exp. Med.*, 201:373-383; Wakkach et al., 2003, *Immunity*, 18:605-617; and Wakkach et al., 2003, *Immunity*, 18:605-617. As demonstrated herein, an increase in the level of p-preDCs in a population of FCs in the presence of a test compound compared to the level of p-preDCs in a population of FCs in the absence of the test compound indicates a compound that is able to improve the ability of donor FCs to facilitate engraftment.

In addition to determining the level of p-pre DCs in a population of FCs in the presence of a test compound, the level of natural killer (NK) cells in the population of FCs also can be determined. See, for example, Neipp et al., 1999, *Transplantation*, 68(3):369-78; Huang et al., 2004, *Blood*, 104(3):873-80; and Huang et al., 2005, *Blood*, 175(6):3753-61. As demonstrated herein, the lack of a substantial decrease in the level of NK cells in the population of FCs contacted with the test compound compared to the level of NK cells in a population of FCs not contacted with the test compound indicates a compound that improves the ability of donor FCs to facilitate engraftment.

The invention also provides methods of characterizing the facilitating capability of FCs. The facilitating capability of FCs can be evaluated by determining the level of one or more of the markers associated with FC disclosed herein (e.g., SDF-1 polypeptide, mRNA encoding SDF-1 polypeptide, CXCR4 polypeptide, mRNA encoding CXCR4 polypeptide, P-selectin polypeptide, and mRNA encoding P-selectin polypeptide). The level of one or more of such markers can be used to characterize the facilitating capability of FCs. Detecting nucleic acids and/or polypeptides is described above. In addition, microarray chip technology can be used to detect markers associated with FCs and the facilitating capability of FCs. For example, a microarray can contain, for example, the 3 markers disclosed herein or additional FC markers known in the art. A microarray can contain, for example, 5 markers, 10 markers, 15 markers, or 20 markers associated with FCs or with the facilitatory capability of FCs.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

Animals

Five- to 6-week-old male C57BL/10SnJ (B10; H-2$^b$); B10.BR.SgSnJ (B10.BR; H-2$^k$); C57BL/6 (B6; H-2$^b$); C3H/HeJ (C3H; H-2$^k$); and BALB/cJ (H-2$^d$) mice were purchased from the Jackson Laboratory (Bar Harbor, Me.). Animals were housed in a barrier animal facility at the Institute for Cellular Therapeutics (University of Louisville, Louisville, Ky.) and cared for according to National Institutes of Health animal care guidelines.

Example 2

FL Treatment

Recombinant human FL (kindly provided by Amgen, Thousand Oaks, Calif.) was diluted in 0.1% mouse serum albumin in saline (MSA; Sigma, St Louis, Mo.). Donor B10.BR mice were subcutaneously injected with 10 μg once daily from day 1 to 10. Control mice received saline only.

Example 3

Monoclonal Antibodies

All monoclonal antibodies (mAb) used in this study were purchased from BD Biosciences-Pharmingen (San Diego, Calif.). Stem cell sorting experiments used directly conjugated mAb: stem cell antigen (Sca)-1-phycoerythrin (PE; E13-161.7); c-kit allophycocyanin (APC; 2B8); CD8α fluorescein isothiocyanate (FITC; 53-6.7); Mac-1 FITC (M1/70); B220 FITC (RA3-6B2); Gr-1 FITC (11-26c.2a); β-TCR FITC (H57-597). FC sorting experiments used β-TCR FITC (H57-597); γδ-TCR FITC (GL3); and CD8α PE (53-6.7). Analysis of the composition of subpopulations in sorted FC use CD11c FITC (HL3) for dendritic cells, CD11b FITC (M1/70) for myeloid/macrophages, NK1.1 FITC (PK136) for NK cells, Pan-NK cells FITC (DX5) for NK cells, and CD19 ApC (1D3) for B cells. H-2$K^k$ FITC (AF3-12.1) and H-2$K^b$ PE (AF6-88.5) mAbs were used for assessment of chimerism.

Example 4

HSC and FC Sorting

HSC were prepared as previously described (Huang et al., 2004, *Blood*, 104:873-880). Briefly, BM from the tibias and femurs of mice was reduced to a single cell suspension. Cells were incubated with antibodies against lineage markers (CD8α FITC, Mac-1 FITC, B220 FITC, Gr-1 FITC, β-TCR FITC), anti-Sca-1 PE and anti-c-kit APC for 30 minutes and washed twice. Cells were resuspended in cell sort media (1×HBSS, 25 mM HEPES, 50 μg/ml gentamicin, and 2% FBS, GIBCO, Grand Island, N.Y.) at 2.5 ×$10^6$ cells/ml and HSC sorted by live sterile sorting (FACSVantage, Becton Dickinson, Mountain View, Calif.). Using this method, a subpopulation of HSC, C-$kit^+$/Sca-$1^+$/$lin^-$ (KSL), was obtained. Sorts of <95% purity were not used.

CD8$^+$/TCR$^-$ FC were sorted as previously reported (Huang et al., 2004, *Blood*, 104:873-880). Mobilized PB cells were harvested by cardiac puncture from anesthetized live donors and collected into heparinized tubes. BM and PB were incubated with anti-CD8α PE, anti-β-TCR-FITC, anti-γδ-TCR-FITC mAbs for 30 minutes and washed twice. Cells were resuspended in cell sort media at 2.5×$10^6$ cells/ml.

Example 5

Reconstitution of Allogeneic Recipients with KSL Cells Plus FC-expanded from PB or BM All KSL cells were sorted from untreated B10.BR or B6 mice. FC were sorted from PB or BM of 10 day FL-treated mice, or from the BM of untreated B10.BR or B6 mice as controls. The FC and KSL cells were mixed prior to transplantation. Recipient B10 or C3H mice were conditioned with 950 cGy of total body irradiation (TBI) using a cesium source (Gamma-cell 40, Nordion, Ontario, Canada). 5000 KSL cells were transplanted alone or in combination with 30,000 FC by lateral tail vein injection at least 6 hours after conditioning.

Example 6

Characterization of Chimeras by Flow Cytometry

Flow cytometry was performed monthly on PB to assess donor chimerism. Chimerism was determined by measuring the percentage of donor (B10.BR or B6) or recipient (B10 or C3H)-derived MHC class $1^+$ cells. Briefly, whole blood from recipients was collected into heparinized tubes, and aliquots of 100 μl were stained with anti-H-2$K^b$-FITC and anti-H-2$K^k$-PE for 30 minutes on ice. Red blood cells were lysed with ammonium chloride lysing buffer for 5 minutes at room temperature, then washed twice in FACS medium and fixed in 1% paraformaldehyde. Multilineage chimerism was assessed by staining PB with anti-H-2$K^k$ PE versus anti-CD4, CD8, β-TCR, NK 1.1, anti-Gr-1, or Mac-1 FITC as previously described (Xu et al., 2004, *J. Immunol.*, 172:1463-1471).

Example 7

Skin Grafts

Skin grafts were performed by techniques previously published (Billingham, 1994, *Clin. Transplant.*, 8:289-292). Briefly, full-thickness skin grafts from the tail of B10.BR, B10 and BALB/c mice were harvested. Graft beds were prepared on the lateral thoracic wall, carefully preserving the panniculus carnosum. Three skin grafts (syngeneic, donor, and third party) were placed on each animal. Each graft was separated from the others by a skin bridge of at least 3 mm. Skin grafts were covered by a double layer of petroleum gauze and a cast. The cast was removed after 7 days. Grafts were scored daily for percent rejection. Rejection was defined as complete when no residual viable graft could be detected.

Example 8

Flow Cytometric Analysis of Adhesion Molecule Expression

FC sorted from FL-treated BM and PB were stained with anti-CD106 (VCAM-1) FITC, anti-CD54 (ICAM-1) FITC, anti-CD102 (ICAM-2) FITC, anti-CD62E (E selectin) PE, anti-CD62L (L selectin) PE, anti-CD62P (P-selectin) PE, and anti-CD44 (Pgp-1) FITC mAbs. After staining, cells were analyzed on a FACSCalibur with CellQuest software (Becton Dickinson). Isotype-specific controls were analyzed on gated FC.

Example 9

Real-time RT-PCR Analysis for SDF-1 and CXCR4

To analyze SDF-1, CXCR4, and RANTES mRNA levels, total mRNA was isolated from FL-expanded BM-FC, PB-FC, or untreated BM-FC with the RNeasy Mini Kit (Qiagen, Inc., Valencia, Calif.) and was reverse-transcribed with TaqMan Reverse Transcription Reagents (Applied Biosystems, Foster City, Calif.). Detection of SDF-1, CXCR4, RANTES and $β_2$-microglobulin mRNA levels was performed by real-time RT-PCR assay using an ABI PRISM 7000 Sequence Detection System (ABI). A 25-μl reaction mixture contains 12.5 μl of SYBR Green PCR Master Mix, 100 ng of cDNA template, each of the forward and reverse primers shown in Table 1. Reactions were compared to BM-FC from untreated controls.

TABLE 1

Sequences of RT-PCR Primers

| Target | Forward Primer (5'→3') | SEQ ID NO | Reverse Primer (5'→3') | SEQ ID NO |
|---|---|---|---|---|
| SDF-1 | CGT GAG GCC AGG GAA GAG T | 1 | TGA TGA GCA TGG TGG GTT GA | 2 |
| CXCR4 | GAC CGC CTT TAC CCC GAT AG | 3 | GCA GGA CGA GAC CCA CCA T | 4 |
| RANTES | GCA AGT GCT CCA ATC TTG CA | 5 | CTT CTC TGG GTT GGC ACA CA | 6 |
| $\beta_2$-microglobulin | CAT ACG CCT GCA GAG TTA AGC A | 7 | GAT CAC ATG TCT CGA TCC CAG TAG | 8 |

The threshold cycle (Ct), i.e., the cycle number at which the amount of amplified gene of interest reached a fixed threshold, was determined subsequently. Relative quantitation of SDF-1, CXCR4, and RANTES mRNA expression was calculated with the comparative Ct method. The relative quantitation value of target, normalized to an endogenous control $\beta_2$-microglobulin gene and relative to a calibrator, is expressed as $2^{-\Delta\Delta Ct}$ (fold difference), where $\Delta Ct=Ct$ of target genes (SDF-1, CXCR4, RANTES)-Ct of endogenous control gene ($\beta_2$-microglobulin), and $\Delta\Delta Ct=\Delta Ct$ of samples for target gene-$\Delta Ct$ of calibrator for the target gene.

Example 10

SDF-1 Migration Assays

Migration of KSL cells to supernatant (SN) from FL-mobilized PB-FC in the presence of an SDF-1 gradient was performed as previously described (Reca et al., 2003, *Blood*, 101:3784-3793). Briefly, HSC were loaded in the upper chamber and SN which had been collected after overnight culture of sorted FC added to the upper chamber to detect priming by the SN.

Example 11

Adhesion Assays

Confluent monolayers of BM stroma cells were established in 24-well plates and grown in IMDM (GIBCO) supplemented with 12.5% horse serum and 12.5% FBS (GIBCO) as previously described (Chilton et al., 2004, *Blood*, 105:2189-2197). Sca-1+ cells from BM were seeded on the stromal cell layers for 1 or 4 hours. Cells were harvested by trypsin digestion, washed, and resuspended in methylcellulose supplemented with murine IL-3 and GM-CSF (Stem Cell Technologies, Vancouver, Canada). On day 7, the number of CFU-GM colonies was scored using an inverted microscope.

Example 12

Colony Forming Cell Assay (CFC)

KSL cells were cultured at a 1:3 ratio with FC from PB or BM from 10 day FL-treated animals in methylcellulose containing mouse growth factors (MethoCult GF M3434, Stem-Cell Technologies), in duplicate at 37° C.-5% $CO_2$-humidified atmosphere (Chilton et al., 2004, *Blood*, 105:2189-97). After 14 days, culture colonies containing more than 50 cells were scored.

Example 13

FL Administration Expands FC in PB and BM

The effect of FL administration on the expansion and mobilization of FC in mice was first evaluated. B10.BR mice were treated with FL daily for 10 days, and the absolute number and proportion of FC in BM and PB were evaluated. The maximum increase in FC was observed after 10 days of FL-treatment, as compared with control mice (FIG. 1). The absolute number as well as relative proportion of FC in PB (FIG. 1A, 1B) and BM (FIG. 1C, 1D) was significantly increased on days 8 and 10 ($P \leq 0.003$), increasing by 100- and 8.5-fold, respectively, at the peak on day 10.

Example 14

Composition of FC in FL-expanded PB Versus BM

The $CD8^+/TCR^-$ FC ($FC_{total}$) is a heterogeneous subpopulation comprised predominantly of $B220^+/CD11c^+/CD11b^-$ cells that resemble p-preDC in function and phenotype. P-preDC are a subpopulation of immature DC shown to be tolerogenic under certain circumstances in vitro. It was recently demonstrated that p-preDC FC are the predominant functional facilitative subset in $FC_{total}$, and removal of p-preDC from FC completely abrogates facilitation. However, p-preDC FC are not as effective at facilitation as $FC_{total}$. P-preDC are expanded and activated by FL, as are FC.

FL PB-FC was therefore compared to FL BM-FC to evaluate the $FC_{total}$ cellular composition. As expected, the number of p-preDC FC was significantly increased in PB-FC, and to a lesser extent BM-FC, after FL treatment. Notably, the number of NK FC remained the same in PB-$FC_{total}$ and was nearly absent in the BM-$FC_{total}$ population after FL treatment. The fact that pre-DC FC are not as potent as $FC_{total}$ suggests that the NK-FC population may be an important collaborative cell in FC total function.

Example 15

FL Expanded PB-FC but not FL-expanded BM FC Enhance Engraftment of Purified Allogeneic HSC It was previously reported that the engraftment-potential of HSC mobilized with FL plus G-CSF or FL alone was superior to HSC obtained from animals treated with G-CSF alone and from normal BM. The function of FL-expanded FC, however, has not previously been evaluated. The function of FL-expanded FC in PB and BM was therefore evaluated.

Figure 2:
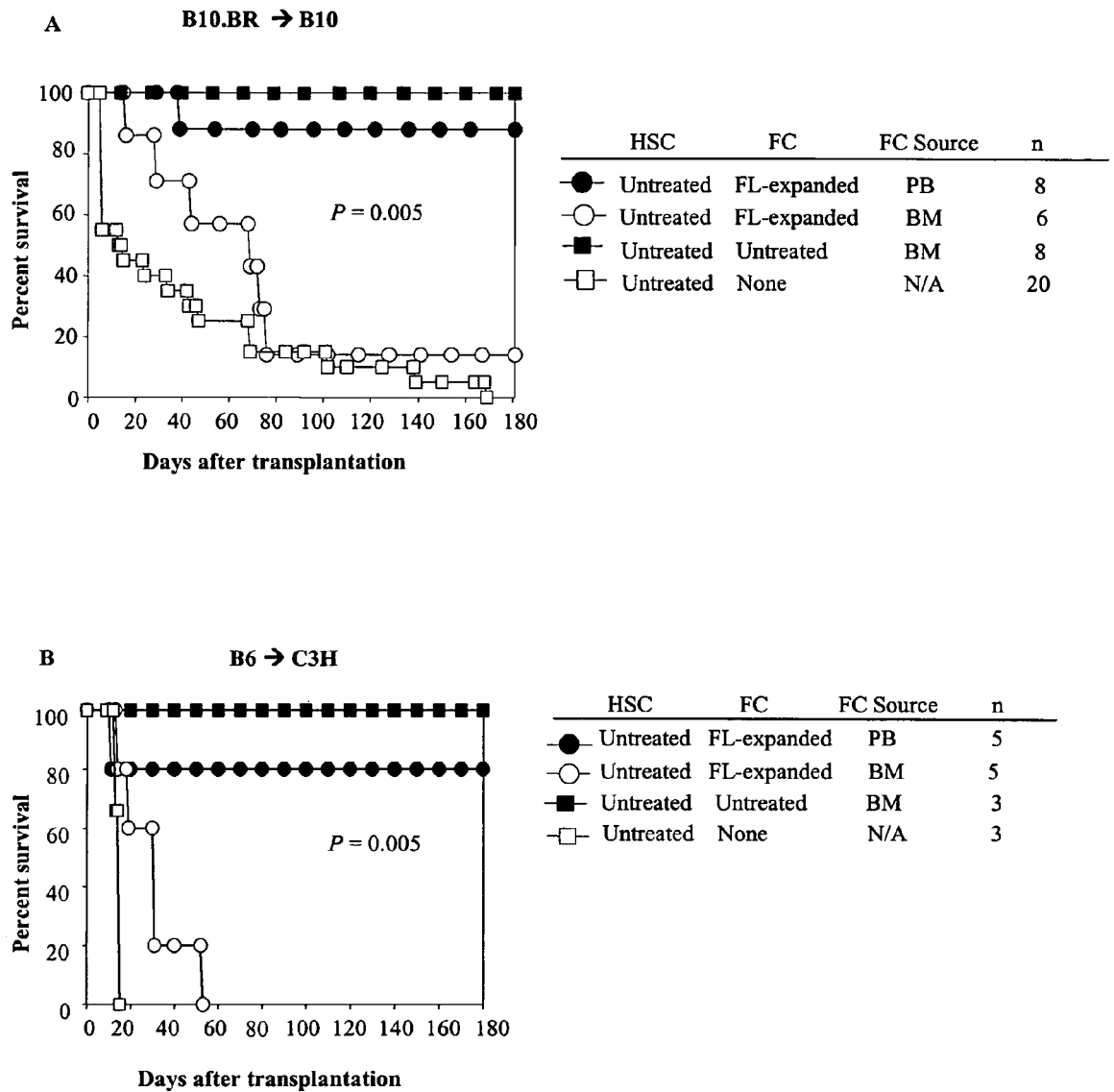
FIG. 2. Kaplan-Meier survival calculation of recipients of KSL cells and FL-expanded FC from PB or BM. Donors were treated once daily with FL (10 μg/mouse/day) for 10 days. Recipients were conditioned with 950 cGy of TBI and transplanted with 5000 KSL cells and 30,000 FC. Results are from a total of 3 experiments. The results from two different strain combinations are shown (B10.BR→B10 [A]; B6→C3H [B]). There was a significant difference in survival between recipients of FL-expanded FC obtained from PB versus BM for both data sets (P=0.005).

FC were sorted from BM or PB of B10.BR mice after 10 days of treatment with FL. Recipient B10 mice were conditioned with 950 cGy of TBI and transplanted with 5000 KSL cells from untreated B10.BR mice plus 30,000 FL-expanded FC. Control B10 mice received 5000 KSL cells alone or 5000 KSL cells plus 30,000 BM FC from untreated B10.BR donors. FL-expanded PB-FC significantly enhanced KSL cells engraftment (P=0.005; FIG. 2A). In striking contrast, FL-expanded BM-FC were significantly impaired in function, with only 14% engrafting.

To exclude a strain-specific effect, similar transplants were carried out using the B6 and C3H strain combination, with similar outcomes (FIG. 2B). Therefore, although FL expands FC in both BM and PB, the PB-FC are significantly superior in facilitating KSL cells engraftment in allogeneic recipients while the FL-expanded BM-FC are impaired in facilitating engragment (P=0.005).

Example 16

Figure 3:
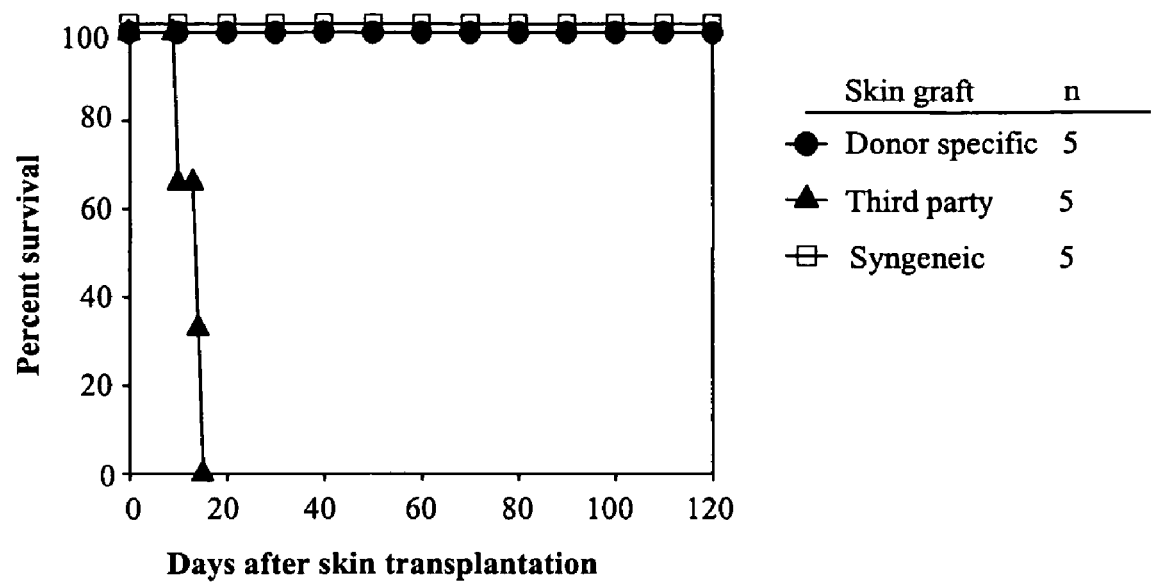
FIG. 3. Facilitated chimeras exhibit tolerance and donor multilineage production. Survival of skin grafts in mixed allogeneic chimeras (B10.BR→B10). Donor-specific (B10.BR), syngeneic (B10), and third-party (BALB/c) skin grafts were transplanted 3 months after HSC transplantation (n=5). Grafts were followed daily.

Recipients of FL-expanded PB-FC Plus HSC Exhibit Functional Tolerance to Donor-specific Skin Allografts To test whether the chimerism achieved with transplantation of KSL cells plus FL-expanded PB-FC induced donor-specific tolerance, skin grafts from B10.BR (KSL donor specific), B10 (syngeneic) and BALB/c (MHC-disparate third-party) mice were performed. Donor-specific skin grafts, both allogeneic and syngeneic, were accepted by chimeras (median survival time (MST)≧120 days), while third-party grafts were promptly rejected (MST=15 days) (FIG. 3).

Recipients of FL-expanded PB FC were analyzed for donor multilineage production at 3 months by flow cytometry. Staining was performed for CD4$^+$, CD8$^+$, and αβ-TCR$^+$ T cells, NK cells, B cells, macrophages, and granulocytes. All recipients analyzed (n=11) exhibited donor multilineage production.

Example 17

FL Increases P-selectin Expression and Downregulates VCAM-1 on PB-FC

Adhesive interactions are critical to the regulation of hematopoiesis and the homing of stem cells after transplantation. A number of cell adhesion molecules (CAM) have been identified that regulate homing and adhesion of HSC to bone marrow stroma, most notably, VCAM-1, ICAM-1, ICAM-2, E-selectin, P-selectin and CD44. See, for example, Simmons et al. (1997, *Clin. Haematol.*, 10:485-505); Verfaillie (1998, *Blood*, 92:2609-12); Verfaillie et al. (1990, *J. Exp. Med.*, 172:509-20); and Frenette et al. (1998, *PNAS USA*, 95:14423-8).

The difference in expression was therefore compared between the three sources of FC: normal marrow FC, FL-expanded BM-FC, and FL-expanded PB-FC for VCAM-1, ICAM-1, ICAM-2, E-selectin, L-selectin, P-selectin, and CD44. CD8$^+$/TCR$^-$ FC were sorted, then stained for adhesion marker expansion. There was a significant (P=0.015) increase in expression of P-selectin on FL-expanded PB-FC compared with the other two groups. To a lesser extent, a larger proportion of FC from PB expressed L-selectin compared to control BM-FC and FL-expanded BM-FC. The other molecules of interest were not significantly different between the groups except that VCAM-1 was decreased in FL-treated PB-FC compared to BM-FC and FL-treated BM-FC.

Example 18

FL-expanded PB-FC Exhibit Significantly Increased Levels of Transcripts for SDF-1 and CXCR4

SDF-1 plays an important role in HSC homing. See, for example, Broxmeyer et al., 1999, *Ann. N.Y. Acad. Sci.*, 872: 142-62. CXCR-4, the receptor for SDF-1, is expressed on HSC, and is believed to be the central mechanism by which HSC migrate to the SDF-1-producing stroma after transplantation.

In order to evaluate the mechanism for impaired FL-expanded BM-FC function and enhanced FL PB-FC function, the presence or absence of these molecules in the different FC populations was evaluated in order to test the hypothesis that FC act as a collaborative cell and co-migrate with HSC after transplantation and during mobilization.

Figure 4:
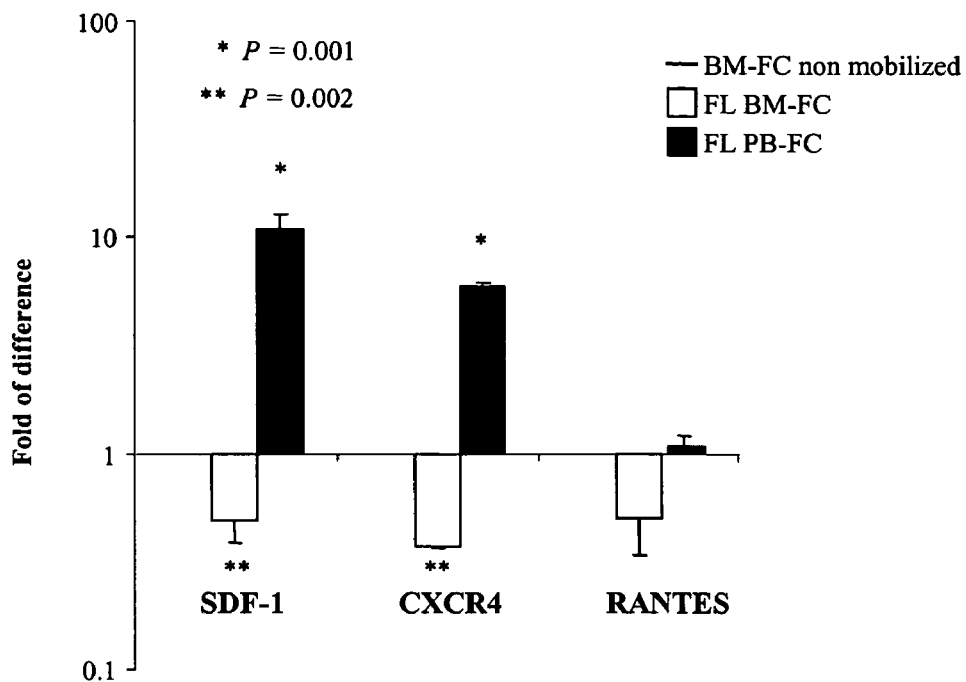
FIG. 4. CXCR4 and SDF-1 are present in FC. (A) Transcript for SDF-1 and CXCR4 are upregulated in FL-expanded PB-FC. Changes in expression of mRNA for SDF-1, CXCR4 and RANTES between FL-expanded PB-FC or FL-expanded BM-FC evaluated by real-time RT-PCR. The data are combined from 2 independent experiments. * P=0.001 or ** P=0.002 compared to purified FC from normal BM. (B) SDF-1 migration assays were performed to evaluate the effect of supernatant from FC to enhance migration of KSL cells. FC-supernatant (SN) was added to the upper chamber with KSL cells and migration to an SDF-1 gradient performed. Data are the mean ±SD of 3 experiments.
Figure 4:
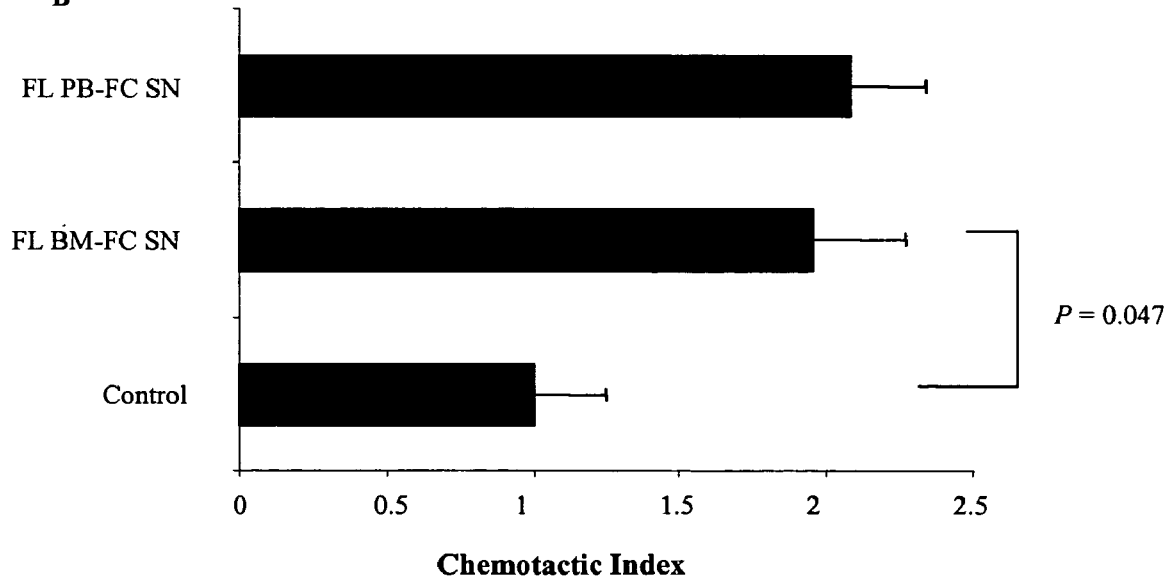

Strikingly, transcripts for SDF-1 and CXCR4 were significantly increased in FL-expanded PB-FC compared to control FC obtained from BM of untreated donors (P=0.001; FIG. 4A). Moreover, the expression of these transcripts was significantly decreased in the less potently functional FL-expanded BM-FC compared to control BM-FC (P=0.002) and FL-expanded PB-FC.

To examine whether FC enhance or prime migration of HSC to an SDF-1 gradient, supernatant from FC collected after overnight culture was added to the upper chamber with KSL cells and migration assays performed. Controls consisted of medium alone. Notably, FC SN significantly enhanced migration of KSL cells compared to controls, confirming the production of protein product of SDF-1 by FC (FIG. 4B).

Example 19

Effect of FL-expanded FC on HSC Adhesion

Another important step in the complex process of HSC engraftment after transplantation is adhesion to stroma in the hematopoietic microenvironment. Adhesion of HSC to stroma cell monolayers correlates with HSC engraftment, at least in vitro.

To evaluate whether the enhanced function of FL-expanded PB-FC versus FL-expanded BM-FC is due to a change in adhesive interactions between FC and HSC, sorted FC were mixed with Sca-1$^+$ cells from BM and co-incubated overnight or placed immediately in adhesion assays. The collected cells were then placed in methylcellulose and CFU-GM colonies enumerated. There was no significant difference in CFU-GM between FL-expanded BM-FC and Sca-1$^+$ cells from BM compared to FL-expanded PB-FC and Sca-1$^+$ cells from BM when the cells were immediately subjected to the adhesion assay (FIG. 5A).

Figure 5:
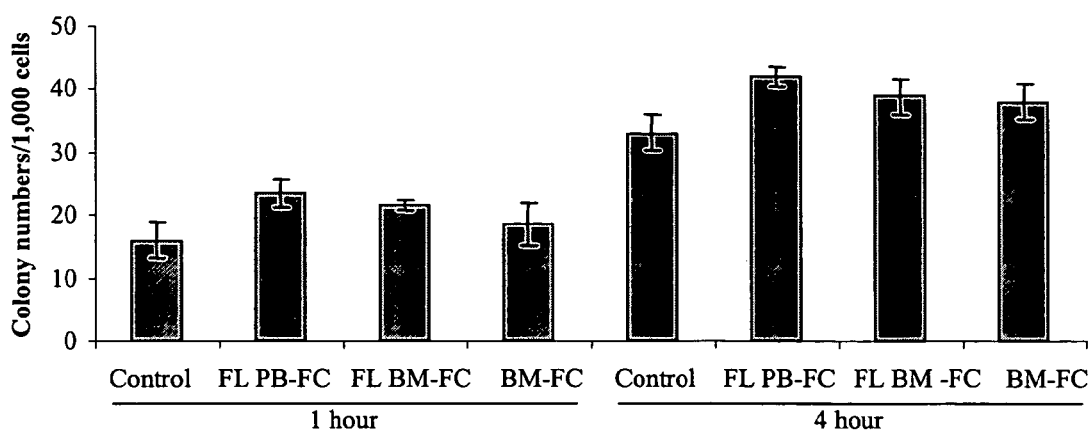
FIG. 5. Adhesion and CFC assays. (A) HSC were incubated for 1 or 4 hours on primary stroma. Adherent cells were then placed in methylcellulose assays and counted 7 days later. Data represent 2 experiments performed in triplicate (P>0.01). Sca-1$^+$ BMC with or without FC were immediately subjected to adhesion assay. Adherent cells were then placed in CFU-GM assays. (B) Sca-1$^+$ BMC were co-incubated with FC overnight, and then subjected to adhesion assay. Controls consisted of HSC alone. (C) FC were sorted from FL-treated donors from BM and PB and placed in CFC with BM Sca-1$^+$ BMC from unmanipulated donors. Each experiment was performed in duplicate and repeated 2 times. All 3 FC populations enhanced HSC clonogenicity.
Figure 5:
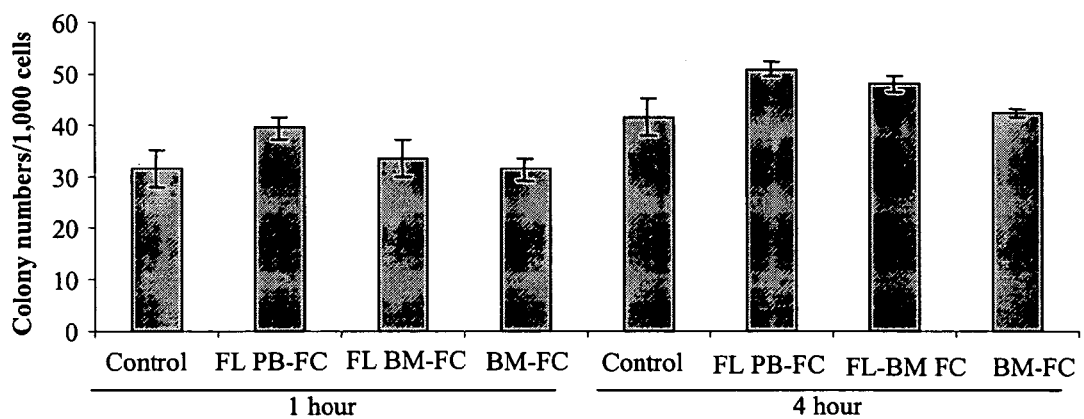

Similarly, no difference was detected between the ability of the three sources of FC to maintain clonogenicity after overnight culture followed by adhesion and CFU-GM colony enumeration (FIG. 5B). Taken together, these data suggest that the disparity in facilitative function between FL-expanded PB-FC and FL-expanded BM-FC is not due to a change in FC-mediated adhesion of HSC to stroma.

Example 20

FL-expanded PB-FC and BM-FC Increase HSC Clonogenicity

Figure 5C:
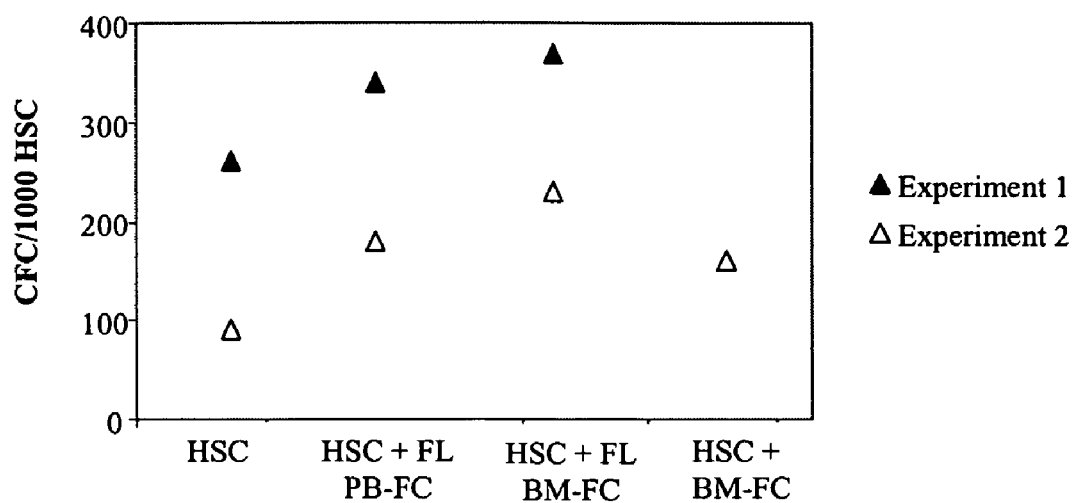

FC have been reported to increase HSC clonogenicity by exerting an anti-apoptotic effect on HSC. Using the colony forming cell (CFC) assay, the impact of FL-expanded PB-FC and FL-expanded BM-FC on HSC colony formation was compared. There was no significant difference between FL-expanded PB-FC and FL-expanded BM-FC compared to BM-FC performed as controls, as cells from both compartments enhanced HSC clonogenicity (FIG. 5C).

Example 21

The Function of BM-FC is Restored 5 Days After Cessation of FL Treatment

Figure 6:
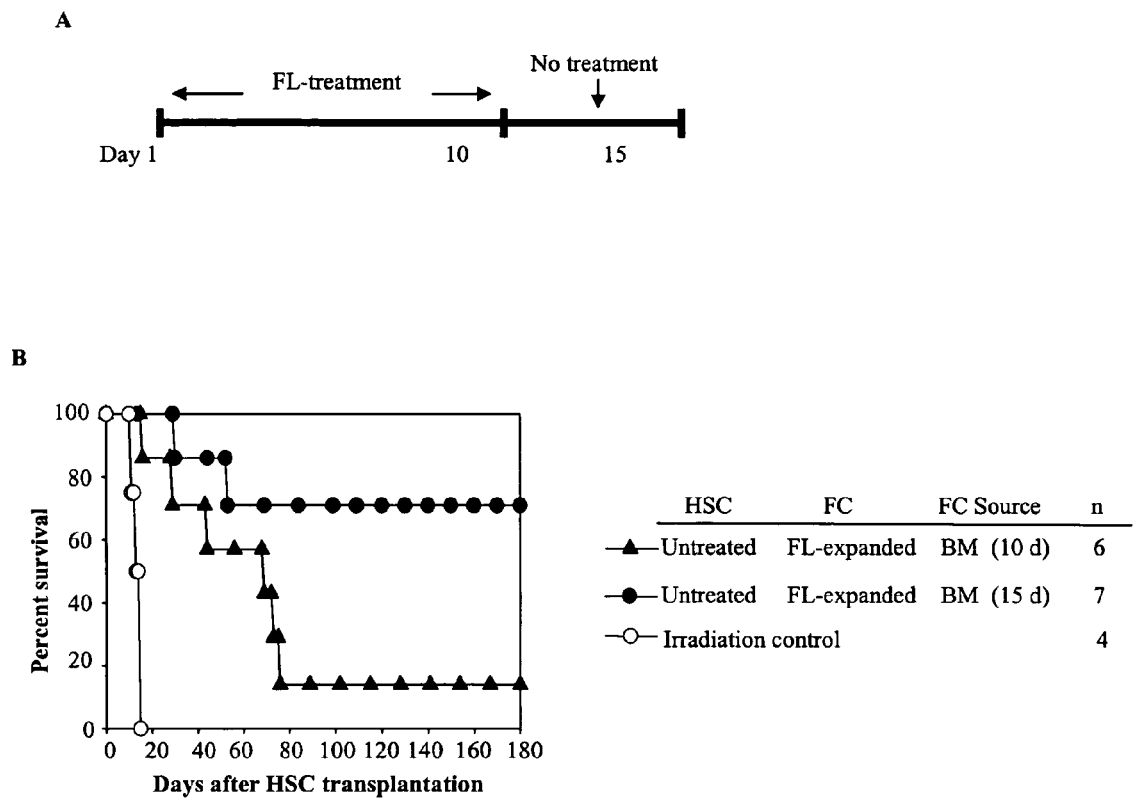
FIG. 6. The function of BM-FC is restored 5 days after cessation of treatment. (A) B10 recipient mice conditioned with 950 cGy TBI and given 5,000 allogeneic Sca-1$^+$ BMC from untreated B10.BR donors either mixed with 30,000 purified FC from FL-treated BM or from BM 5 days after treatment ends. (B) A Significant difference in survival was observed between recipients of FC obtained from FL-expanded BM (n=6) versus BM 5 days after treatment ends (n=7; P=0.04), suggesting that the changes which occur due to FL treatment are quite rapidly restored in the BM compartment.

To evaluate the duration of impaired function of FL-expanded BM-FC, B10.BR mice were treated with a 10 day course of FL. Five days after cessation of growth factor treatment, B10 recipient mice were conditioned with 950 cGy TBI and transplanted with 5,000 KSL cells from untreated B10.BR donors mixed with 30,000 FC from BM from 10 day versus day 15. Significantly enhanced facilitation occurred in the recipients of FL-expanded BM-FC harvested 5 days after cessation of FL treatment (P=0.04) compared to FC harvested on day 10 of FL-treatment (FIG. 6).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of screening for a compound that increases the amount of SDF-1 polypeptide or mRNA encoding said SDF-1 polypeptide in facilitatory cells (FCs), comprising:
  contacting FCs with a test compound; and
  determining the amount of SDF-1 polypeptide or mRNA encoding said SDF-1 polypeptide in said FCs,
  wherein an increase in said amount of SDF-1 polypeptide or mRNA encoding said SDF-1 polypeptide in FCs contacted with said test compound compared to an amount of SDF-1 polypeptide or mRNA encoding said SDF-1 polypeptide in FCs not contacted with said test compound is indicative of a compound that increases the amount of SDF-1 polypeptide or mRNA encoding said SDF-1 polypeptide in said FCs.

2. The method of claim 1, wherein said determining step is nucleic acid based.

3. The method of claim 2, wherein said nucleic acid based determining step is RT-PCR.

4. The method of claim 1, wherein said determining step is polypeptide based.

5. The method of claim 4, wherein said polypeptide-based determining step is an immunoassay.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide

<400> SEQUENCE: 1
cgtgaggcca gggaagagt                                                  19

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
tgatgagcat ggtgggttga                                                 20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
gaccgccttt accccgatag                                                 20

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide

<400> SEQUENCE: 4
gcaggacgag acccaccat                                                  19

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 5
gcaagtgctc caatcttgca                                                    20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cttctctggg ttggcacaca                                                    20

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
catacgcctg cagagttaag ca                                                 22

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide

<400> SEQUENCE: 8
gatcacatgt ctcgatccca gtag                                               24
```